United States Patent [19]

Davis

[11] Patent Number: 4,584,115
[45] Date of Patent: Apr. 22, 1986

[54] METHOD OF PREPARING BORON-CONTAINING COMPOSITIONS USEFUL AS LUBRICANT ADDITIVES

[75] Inventor: Kirk E. Davis, Euclid, Ohio

[73] Assignee: The Lubrizol Corporation, Wickliffe, Ohio

[21] Appl. No.: 429,894

[22] Filed: Sep. 30, 1982

Related U.S. Application Data

[63] Continuation-in-part of Ser. No. 347,762, Feb. 11, 1982, abandoned, which is a continuation-in-part of Ser. No. 267,239, May 26, 1981, abandoned.

[51] Int. Cl.[4] ........................ C10M 1/20; C10M 1/54
[52] U.S. Cl. ............................... 252/49.6; 252/389.4; 568/1
[58] Field of Search ................ 252/42.7, 49.6, 389.4; 568/1

[56] References Cited

U.S. PATENT DOCUMENTS

| 3,288,710 | 11/1966 | Hollitz | 252/49.6 X |
| 3,316,287 | 4/1967 | Nunn et al. | 252/49.6 X |
| 4,035,403 | 7/1977 | Gough et al. | 260/429.7 |

FOREIGN PATENT DOCUMENTS 48-14627  2/1973  Japan.
931000   7/1963  United Kingdom.

*Primary Examiner*—W. J. Shine
*Attorney, Agent, or Firm*—Walter C. Danison, Jr.; Denis A. Polyn; Forrest L. Collins

[57] ABSTRACT

Reaction products of boric acid or boron trioxide with an epoxide having at least 8 carbon atoms (especially a straight-chain aliphatic epoxide) are useful anti-wear, friction modifying and rust inhibiting additives for lubricants. They are particularly useful in lubricants containing relatively large amounts of basic alkaline earth metal phenates or salicylates and/or free hydroxy group-containing alkenylsuccinic acid ester dispersants.

20 Claims, No Drawings

METHOD OF PREPARING BORON-CONTAINING COMPOSITIONS USEFUL AS LUBRICANT ADDITIVES

CROSS REFERENCE TO RELATED APPLICATIONS

This application is a continuation-in-part of copending application Ser. No. 347,762, filed Feb. 11, 1982, now abandoned, which is a continuation-in-part of co-pending application Ser. No. 267,239, filed May 26, 1981, now abandoned.

BACKGROUND OF INVENTION

This invention relates to compositions of matter useful as additives for lubricants, to a method for their preparation, and to additive concentrates and lubricants containing them. In one embodiment, the invention includes oil-soluble boron-containing compositions prepared by reacting boric acid or boron trioxide with an epoxide having at least eight carbon atoms.

The increasing sophistication of internal combustion engines necessitates the development of new types of lubricants for use in them. The new engines in many instances operate under far more severe conditions than was formerly the case, and the lubricants must be tailored so as to permit them to be used over prolonged periods of time under those severe conditions.

As an example of the diverse types of requirements for lubricants, consideration should be given to diesel engines in heavy machinery. The lubricant performance requirements in such engines are much different from those in gasoline engines for automobiles. Nevertheless, it is frequently advantageous to formulate a single multipurpose lubricant for use in both types of engines.

The severity of the conditions in diesel heavy machinery engines requires the presence in the lubricant of relatively high levels of ashless dispersants and/or ash-producing detergents. For example, many such lubricants contain basic alkaline earth metal phenates in amounts of 2.5% by weight or higher, and/or free hydroxy group-containing alkenylsuccinic acid ester dispersants in amounts of 1.5% or higher. The use of such lubricants in ordinary gasoline engines frequently causes a high degree of wear on engine parts. Conventional anti-wear agents such as zinc dialkylphosphorodithioates are, in many instances, not entirely effective in eliminating this problem.

Resinous products obtained by reacting 0.1 to 4 parts by weight of boron trioxide with one part of a monoepoxide compound having a boiling point above 50° C. are described in UK Patent No. 931,000. The preparation of oil soluble surface active organic boron compound by reacting one mole of boric acid with from one to two moles of alphaolefin oxide having 10 to 32 carbon atoms in the presence of water is described in Japanese Appln. No. 48/14627 and abstracted in *Chemical Abstracts*, 95, 99685y (1981).

SUMMARY OF INVENTION

This invention relates to boron-containing compositions prepared by reacting, at a temperature of from about 80° to about 250° C.,
(A) at least one of boric acid or boron trioxide with
(B) at least one epoxide having the formula

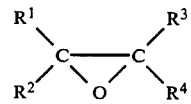

wherein each of $R^1$, $R^2$, $R^3$ and $R^4$ is hydrogen or an aliphatic radical, or any two thereof together with the epoxy carbon atom or atoms to which they are attached, form a cyclic radical, said epoxide containing at least 8 carbon atoms, in the presence of a minor amount of a heel of a previously obtained oil-soluble boron-containing composition prepared by reacting reagents A and B.

The invention also relates to the use of these and similar boron compounds as lubricant additives.

DESCRIPTION OF THE PREFERRED EMBODIMENTS

The boron compositions of this invention are characterized by the method for their preparation which involves the reaction of two materials (reagents A and B) in the presence of a minor amount of a heel of a previously obtained oil-soluble boron containing composition prepared by reacting reagents A and B. The additive concentrates and lubricant of the invention may contain the boron-containing compositions prepared in the presence or absence of the heel.

Reagent A may be boron trioxide or any of the various forms of boric acid, including metaboric acid ($HBO_2$), orthoboric acid ($H_3BO_3$) and tetraboric acid ($H_2B_4O_7$). Boric acid, and especially orthoboric acid, is preferred.

Reagent B is at least one epoxide having the above formula and containing at least 8 carbon atoms. In the formula, each of the R values is most often hydrogen or an aliphatic radical with at least one being an aliphatic radical containing at least 6 carbon atoms. The term "aliphatic radical" includes aliphatic hydrocarbon radicals (e.g., hexyl, heptyl, octyl, decyl, dodecyl, tetradecyl, stearyl, hexenyl, oleyl), preferably free from acetylenic unsaturation; substituted aliphatic hydrocarbon radicals including substituents such as hydroxy, nitro, carbalkoxy, alkoxy and alkylthio (especially those containing a lower alkyl radical; i.e., one containing 7 carbon atoms or less); and hetero atom-containing radicals in which the hetero atoms may be, for example, oxygen, nitrogen or sulfur. The aliphatic radicals are preferably alkyl radicals, and more preferably those containing from about 10 to about 20 carbon atoms. It is within the scope of the invention to use commercial mixtures of epoxides; for example, commercial mixtures of $C_{14-16}$ or $C_{14-18}$ epoxides and the like, wherein $R^1$ is a mixture of alkyl radicals having two less carbon atoms than the epoxide. Most desirably, $R^1$ is a straightchain alkyl radical and especially the tetradecyl radical.

Also within the scope of the invention is the use of epoxides in which any two of the R radicals together with the epoxy carbon atom or atoms to which they are attached, form a cyclic radical, which may be alicyclic or heterocyclic. Examples are n-butylcyclopentene oxide, n-hexylcyclohexene oxide, methylenecyclooctene oxide and 2-methylene-3-n-hexyltetrahydrofuran oxide.

The boron-containing compositions may be prepared by merely blending the two reagents and heating them at a temperature from about 80° to about 250° C., preferably from about 100° to about 200° C., for a period of time sufficient for reaction to take place. If desired, the reaction may be effected in the presence of a substantially inert, normally liquid organic diluent such as toluene, xylene, chlorobenzene, dimethylformamide or the like, but such diluents are usually unnecessary. During the reaction, water is frequently evolved and may be removed by distillation.

In a preferred method for preparing the boron-containing compositions, which minimizes foaming and exothermic reactions which generate heat faster than is desirable, the reaction of reagents A and B is conducted in the presence of a "heel" of a product. A "heel" is a portion of the product of a previous reaction of reagents A and B. The reagent A which is blended with the "heel" may be similar to or different from reagent A used to prepare the heel. Generally, however, it is preferred that reagent A added to the heel is identical to reagent A used to form the heel. Reagent B which is added to the heel may be similar to or different from reagent B used to form the heel. However, it is preferred that reagent B which is added to the blend of reagent A and the "heel" is similar to or identical to the reagent B used in preparing the heel. The molar ratio of reagents A and B added to the heel may be the same as or different from the molar ratio of reagents A and B used to form the heel, but in all instances the molar ratio will be between about 1:0.25 and about 1:4. Generally reagent A is initially blended with a "heel" of product. The blend is heated to the desired reaction temperature, typically between about 150° and about 200° C., and reagent B is added gradually as water of reaction is removed. Alternatively the water of reaction formed on heating blend of the heel and reagent A may be removed by distillation at elevated temperature before reagent B is added to the blend. Heating is still required to remove additional water of reaction formed after reagent B is added.

The molar ratio of reagent A to reagent B is generally between about 1:0.25 and about 1:4. Ratios between about 1:1 and about 1:3 are preferred, with 1:2 being an especially preferred ratio.

It is frequently advantageous to employ a catalytic amount of an alkaline reagent to facilitate the reaction of reagents A and B. Suitable alkaline reagents include inorganic bases and basic salts such as sodium hydroxide, potassium hydroxide and sodium carbonate; metal alkoxides such as sodium methoxide, potassium t-butoxide and calcium ethoxide; heterocyclic amines such as piperidine, morpholine and pyridine; and aliphatic amines such as n-butylamine, di-n-hexylamine and tri-n-butylamine. The preferred alkaline reagents are the aliphatic and heterocyclic amines and especially tertiary amines. When the preferred method involving the "heel" is used, the alkaline reagent is typically added to the blend of the "heel" with reagent A.

The molecular structures of the compositions of this invention are not known with certainty. During their preparation water is evolved in near-stoichiometric amounts for conversion of boric acid to boron trioxide when reagent A is boric acid, and gel permeation chromatography of the composition prepared from boric acid and a $C_{16}$ α-olefin oxide mixture in a 1:2 molar ratio indicates the presence in substantial amounts of three constituents having approximate molecular weights of 400, 600, and 1200. From these facts, it appears that the composition may comprise principally borated condensation products of polymers of the epoxide with a minor proportion of compounds of one or both of the formulas

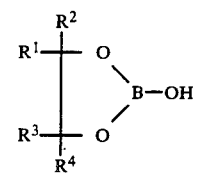

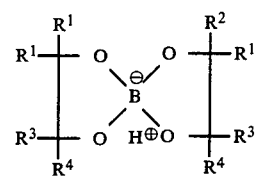

wherein $R^1$, $R^2$, $R^3$ and $R^4$ are as previously defined.

The preparation of the boron compositions useful in this invention is illustrated by the following examples. All parts and percentages are by weight.

EXAMPLE 1

A mixture of 1500 parts (6.25 moles) of 1-hexadecene oxide and 1 part of tri-n-butylamine is heated to 100–110° C. under nitrogen, with stirring. Boric acid, 193 parts (3.13 moles), is added incrementally over 15 minutes. When boric acid addition is complete, the reaction mixture is heated to 185° C. as water is removed by distillation. When water evolution ceases, the mixture is filtered while hot, and the filtrate is allowed to cool to a waxy solid melting at 60–65° C. This solid is the desired product; it contains 2.7% boron.

EXAMPLE 2

Following substantially the procedure of Example 1, 794 parts (3.31 moles) of the epoxide of Example 1 is reacted with 102.6 parts (1.65 moles) of boric acid in the absence of catalysts. The product contains 2.0% boron.

EXAMPLE 3

Following substantially the procedure of Example 2, 2000 parts (8.3 moles) of 1-hexadecene oxide is reacted with 344 parts (5.6 moles) of boric acid. The product is a waxy solid containing 2.37% boron.

EXAMPLE 4

A mixture of 1416 parts (6 moles) of a commercial mixture of $C_{14-16}$ α-olefin oxides, 124 parts (2 moles) of boric acid, 1 part of tri-n-butylamine and 250 parts of xylene is heated under reflux for about 8 hours as water is removed by distillation. After water removal is complete, the xylene is removed by vacuum stripping and the residue is filtered. The product, a light yellow liquid, contains 1.52% boron.

EXAMPLE 5

Boric acid, 81 parts (1.5 moles), is added over two hours at 90°–120° C., to the α-olefin oxide mixture of Example 4. Tri-n-butylamine, 0.15 part, is added at 100° C. and the mixture is heated at 130°–160° C. with stirring for 4 hours. It is then filtered, using a filter aid material. The filtrate, a viscous orange liquid, is the product; it contains 3.61% boron.

EXAMPLE 6

Boron trioxide, 35 parts (0.5 mole), is added over 2 hours, at 100°–130° C., to 118 parts (0.5 mole) of the α-olefin oxide mixture of Example 4. The mixture is then heated to 150° C. and 0.2 part of tri-n-butylamine is added. An additional 118 parts of the epoxide mixture is added and heating is continued for 2 hours. The product is then filtered, using a filter aid material; the filtrate, a viscous orange liquid, is the product. It contains 3.02% boron.

EXAMPLE 7

A mixture of 572 parts (2 moles) of 1-octene oxide, 62 parts (1 mole) of boric acid and 100 parts of toluene is heated under reflux for 18 hours as water is removed by distillation. The mixture is then vacuum stripped and the residue is filtered, using a filter aid material. The filtrate, an amber liquid, is the desired product; it contains 2.22% boron.

EXAMPLE 8

A blend of 193 parts (3.13 moles) of boric acid, 1 part of tri-n-butylamine and a "heel" comprising 402 parts of the product prepared as in Example 1 is heated to 188° C., with stirring, as volatiles are removed by distillation. After 8½ hours, 1500 parts (6.25 moles) of 1-hexadecene oxide is added over 5½ hours at 186°–195° C., with stirring. Heating and stirring are continued for two hours as volatiles are removed. The material is then vacuum stripped and filtered at 93°–99° C. The filtrate is the desired product; it contains 2.12% boron.

EXAMPLE 9

A mixture of 1500 parts (6.25 moles) of 1-hexadecene oxide and 1 part of tri-n-butylamine is heated with stirring to 100°–110° C. under nitrogen. Boric acid (386 parts, 6.25 moles) is added incrementally over a period of 15 minutes. When the boric acid addition is completed, the reaction mixture is heated to 185° C., as water is removed by distillation. When water evolution ceases, the mixture is filtered while hot, and the filtrate is allowed to cool.

EXAMPLE 10

A blend of 775 parts (12.5 moles) of boric acid and 944 parts of a "heel" of the product(filtrate) obtained in Example 9, is heated to 185° C. under nitrogen, as volatiles are removed by distillation. 1-Hexadecene oxide, 3000 parts (12.5 moles), is added incrementally over 2½ hours 180°–185° C. Heating is continued until removal of volatiles is complete. The residue is then vacuum stripped and filtered. The filtrate is the desired product; it contains 3.9% boron.

EXAMPLE 11

The procedure of Example 10 is repeated except that the "heel" used is a heel of the product obtained in Example 1.

As previously indicated, the boron-containing compositions of this invention are useful as additives for lubricants. They are particularly effective in reducing wear which may result from the use in heavy-duty or multipurpose lubricants of high levels of ashless or ash-producing dispersants and detergents. They are also effective as friction modifiers, rust inhibitors and fuel economy additive in motor oils.

The compositions of this invention can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metal-working lubricants, hydraulic fluids and other lubricating oil and grease compositions may also benefit from the incorporation therein of the compositions of the present invention.

Natural oils include liquid petroleum oils and solvent-treated or acid-treated mineral lubricating oils of the paraffinic, naphthenic and mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1-decenes), etc. and mixtures thereof]; alkylbenzenes [e.g., dodecylbenzenes, tetradecylbenzenes, dinonylbenzenes, di(2-ethylhexyl)benzenes, etc.]; polyphenyls (e.g., biphenyls, terphenyls, alkylated polyphenyls, etc.), alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic lubricating oils. These are exemplified by the oils prepared through polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, tripentaerythritol, etc.

Silicon-based oils such as the polyalkyl-, poly- aryl-, polyalkoxy-, or polyaryloxy-siloxane oils and silicate oils comprise another useful class of synthetic lubricants [e.g., tetraethyl silicate, tetraisopropyl silicate, tetra-(2-ethylhexyl) silicate, tetra-(4-methyl-2-ethylhexyl) silicate, tetra-(p-tert-butylphenyl) silicate, hexa(4-methyl-2-pentoxy)-disiloxane, poly(methyl)-siloxanes, poly(methylphenyl)-siloxanes, etc.]. Other synthetic lubricating oils include liquid esters of phosphorus-containing acids (e.g., tricresyl phosphate, trioctyl phosphate, diethyl ester of decylphosphonic acid, etc.) polymeric tetrahydrofurans and the like.

Unrefined, refined and rerefined oils (and mixtures thereof) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Generally, the lubricants of the present invention contain an amount of the boron containing compositions described above sufficient to provide it with antiwear, friction modifying and/or rust inhibiting properties. Normally this amount will be about 0.01 to about 10%, preferably about 0.1 to about 5%, of the total weight of the lubricant. The concentrates and lubricants may contain the boron-containing compositions obtained by reaction of reagent A with reagent B in the presence or absence of a "heel", or the concentrates and lubricants can contain mixtures of such compositions.

The invention also contemplates the use of other additives in combination with the boron-containing compositions. Such additives include, for example, detergents and dispersants of the ash-producing or ashless type, corrosion and oxidation-inhibiting agents, pour point depressing agents, extreme pressure agents, color stabilizers and antifoam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-$\beta$-naphthylamine, and dodecylamine. A particularly effective method for preparing the basic salts comprises mixing an acid with an excess of a basic alkaline earth metal neutralizing agent and at least one alcohol promoter, and carbonating the mixture at elevated temperatures (60°–200° C.).

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogen-containing compounds such as amine, organic hydroxy compounds such as phenols and alcohols, and/or basic inorganic materials. Examples of these "carboxylic dispersants" are described in British Pat. No. 1,306,529 and in many U.S. patents including the following:

| | | |
|---|---|---|
| 3,163,603 | 3,351,552 | 3,541,012 |
| 3,184,474 | 3,381,022 | 3,542,678 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | 4,234,435 |
| 3,346,493 | 3,522,179 | Re 26,433 |

(2) Reaction products of relatively high molecular weight aliphatic or alicyclic halides with amines, preferably polyalkylene polyamines. These may be characterized as "amine dispersants" and examples thereof are described for example, in the following U.S. Pat. Nos.

| | |
|---|---|
| 3,275,554 | 3,454,555 |
| 3,438,757 | 3,565,804 |

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. Pat. Nos. are illustrative:

| | | |
|---|---|---|
| 2,459,112 | 3,442,808 | 3,591,598 |
| 2,962,442 | 3,448,047 | 3,600,372 |
| 2,984,550 | 3,454,497 | 3,634,515 |
| 3,036,003 | 3,459,661 | 3,649,229 |
| 3,166,516 | 3,461,172 | 3,697,574 |
| 3,236,770 | 3,493,520 | 3,725,277 |
| 3,355,270 | 3,539,633 | 3,725,480 |
| 3,368,972 | 3,558,743 | 3,726,882 |
| 3,413,347 | 3,586,629 | 3,980,569 |

(4) Products obtained by post-treating the carboxylic amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.:

| | | | |
|---|---|---|---|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,522 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Pat. Nos.:

| | |
|---|---|
| 3,329,658 | 3,666,730 |
| 3,449,250 | 3,687,849 |
| 3,519,565 | 3,702,300 |

The above-noted patents are incorporated by reference herein for their disclosures of ashlets dispersants.

Particularly preferred lubricants of this invention are those containing the boron-containing composition in a combination with at least one of (i) basic alkaline earth metal sulfonate, carboxylate or phenate detergents in the amount of at least 2.5% by weight and (ii) ashlesstype detergents and dispersants, those derived from alkenylsuccinic acid and amines or organic hydroxy compounds in the amount of at least 1.5% by weight. When used in such lubricants, the boron-containing compositions cause a significant decrease in engine wear.

Extreme pressure agents and corrosion- and oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearly phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

The compositions of this indention can be added directly to the lubricant. Preferably, however, they are diluted with a substantially inert, normally liquid organic diluent such as mineral oil, naphtha, benzene, toluene or xylene, to form an additive concentrate. These concentrates usually contain from about 5% to about 25% by weight of the composition of this invention and may contain, in addition, one or more other additives known in the art or described hereinabove.

Illustrative concentrates and lubricants of this invention are listed in Table I. All amounts are by weight.

TABLE I

| | |
|---|---|
| Concentrate A | |
| Product of Example 1 | 20 |
| Mineral Oil | 80 |
| Concentrate B | |
| Product of Example 10 | 15 |
| Mineral Oil | 85 |
| Concentrate C | |
| Product of Example 10 | 20 |
| Reaction product of polybutenyl succinic anhydride with ethylene polyamine and pentaerythritol | 10 |
| Mineral Oil | 70 |
| Lubricant D | |
| Product of Example 1 | 2.00 |
| Mineral Oil | 98.00 |
| Lubricant E | |
| Product of Example 10 | 2.00 |
| Reaction product of polybutenyl succinic anhydride with ethylene polyamine and pentaerythritol | 1.80 |
| Basic calcium tetrapropenylphenate | 2.50 |
| Mineral Oil | 95.70 | additional lubricating compositions are shown in Table II.

TABLE II

| | Parts by weight | |
|---|---|---|
| Ingredient | Lubricant F | G |
| Mineral oil | 87.94 | 14.70 |
| Poly-α-olefin-polyol carboxylate synthetic lubricant | — | 74.97 |
| Product of Example 1 | — | 1.00 |
| Product of Example 8 | 1.00 | — |
| Reaction product of polybutenyl succinic anhydride with ethylene polyamine and pentaerythritol | 1.62 | 2.20 |
| Polybutenyl succinic anhydride-ethylene polyamine reaction product | 1.80 | 1.71 |
| Basic magnesium polybutenylsalicylate | — | 3.73 |
| Basic calcium tetrapropenylphenate | 2.56 | — |
| Basic calcium salt of sulfurized tetrapropenylphenol | 1.49 | — |
| Basic calcium petroleum sulfonate | 2.40 | — |

TABLE II-continued

| Ingredient | Parts by weight | |
|---|---|---|
| | Lubricant F | G |
| Ethylene-propylene-diene terpolymer | — | 0.11 |
| Vinyl acetate-vinyl ether-dialkyl fumarate terpolymer | — | 0.20 |
| Zinc dialkylphosphorodithioate | 1.19 | 1.38 |
| Silicone anti-foam agent | 0.011 | 0.011 |
| Total basic alkaline earth metal phenate detergent | 4.05 | — |
| Total hydroxy group-containing alkenyl-succinic acid ester dispersant | 1.62 | 2.20 |

What is claimed is:

1. A method for preparing an oil-soluble boron-containing composition of matter which comprises reacting, at a temperature from about 80° C. to about 250° C.

(A) at least one of boric acid or boron trioxide with (B) at least one epoxide having the formula

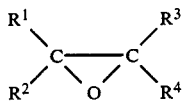

wherein each of $R^1$, $R^2$, $R^3$ and $R^4$ is hydrogen or an aliphatic radical, or any two thereof together with the epoxy carbon atom or atoms to which they are attached, form a cyclic radical, said epoxide containing at least 8 carbon atoms,
wherein the molar ratio of reagents A and B is between about 1:0.25 and about 1:4,; in the presence of a minor amount of a heel of a previously obtained oil-soluble boron-containing composition prepared by reagents A and B in a molar ratio of between about 1:0.25 and about 1:4.

2. The method of claim 1 wherein the reagent A being reacted is the same as the reagent A used in the preparation of the heel.

3. The method of claim 1 wherein th epoxide of reagent B being reacted is the same as the epoxide of reagent B used in the preparation of the heel.

4. The method of claim 1 wherein the reagents A and B being reacted are the same as the reagents A and B used in a preparation of the heel.

5. The method of claim 1 wherein the two molar ratios are the same.

6. The method according to claim 1 wherein each of $R^1$, $R^2$, $R^3$ and $R^4$ is hydrogen or an aliphatic radical, at least one thereof being an aliphatic radical containing at least 6 carbon atoms.

7. The method according to claim 6 wherein $R^1$ is an alkyl radical containing from about 10 to about 20 carbon atoms and $R^2$, $R^3$ and $R^4$ are each hydrogen.

8. The method according to claim 7 wherein reagent A is orthoboric acid.

9. The method according to claim 8 wherein $R^1$ is a straight-chain radical.

10. The method according to claim 9 wherein $R^1$ is the tetradecyl radical.

11. The method of any one of claims 2-4, 5-10 and 1 wherein reagent B is added gradually to a mixture of reagent A and the heel.

12. The method of claim 11 wherein the mixture of reagent A and the heel is heated to remove any water present prior to the addition of reagent B.

13. The method of claim 12 wherein the mixture of reagent A and the heel also contains a catalytic amount of an alkaline reagent.

14. The method of claim 13 wherein the alkaline reagent is an aliphatic amine.

15. The method of claim 13 wherein the alkaline reagent is a tertiary amine.

16. The method of claim 15 wherein the tertiary amine is tri-n-butylamine.

17. The method according to any one of claims 2-4, 5-10 and 1 wherein the reaction is effected in the presence of a catalytic amount of an alkaline reagent.

18. The method according to claim 17 wherein the alkaline reagent is an aliphatic amine.

19. The method according to claim 18 wherein the amine is a tertiary amine.

20. The method according to claim 19 wherein the amine is tri-n-butylamine.

* * * * *